(12) United States Patent
Yamada et al.

(10) Patent No.: US 8,970,839 B2
(45) Date of Patent: *Mar. 3, 2015

(54) DETECTION DEVICE

(75) Inventors: Kohei Yamada, Minowa (JP);
Yoshifumi Hano, Suwa (JP)

(73) Assignee: Seiko Epson Corporation (JP)

( * ) Notice: Subject to any disclaimer, the term of this patent is extended or adjusted under 35 U.S.C. 154(b) by 130 days.

This patent is subject to a terminal disclaimer.

(21) Appl. No.: 13/441,374

(22) Filed: Apr. 6, 2012

(65) Prior Publication Data

US 2012/0257198 A1  Oct. 11, 2012

(30) Foreign Application Priority Data

Apr. 8, 2011 (JP) ................. 2011-085927

(51) Int. Cl.
*G01J 3/44* (2006.01)
*G01N 21/65* (2006.01)

(52) U.S. Cl.
CPC .................... *G01N 21/658* (2013.01)
USPC ....................................... 356/301

(58) Field of Classification Search
USPC .............. 356/301, 436, 437, 440–442, 445
See application file for complete search history.

(56) References Cited

U.S. PATENT DOCUMENTS

| | | | | |
|---|---|---|---|---|
| 5,328,851 A | * | 7/1994 | Zaromb | 436/178 |
| 6,649,416 B1 | | 11/2003 | Kauer et al. | |
| 2007/0108126 A1 | * | 5/2007 | Lee | 210/635 |
| 2009/0143659 A1 | | 6/2009 | Li et al. | |
| 2010/0053605 A1 | * | 3/2010 | Ragucci et al. | 356/301 |
| 2010/0101983 A1 | | 4/2010 | Butler et al. | |
| 2010/0116021 A1 | * | 5/2010 | O'Brien | 73/23.37 |
| 2010/0267013 A1 | * | 10/2010 | Su et al. | 435/6 |
| 2011/0311978 A1 | | 12/2011 | Makarewicz, Jr. et al. | |

FOREIGN PATENT DOCUMENTS

| | | |
|---|---|---|
| JP | 2000-356587 | 12/2000 |
| JP | 2005-265634 A | 9/2005 |
| JP | 3714671 | 9/2005 |
| JP | 2006-003285 A | 1/2006 |
| JP | 2006-258636 | 9/2006 |
| JP | 2006-266906 | 10/2006 |
| JP | 2007-078620 A | 3/2007 |
| JP | 2007-101476 | 4/2007 |

* cited by examiner

*Primary Examiner* — Tri T Ton
*Assistant Examiner* — Willie Merrell, II
(74) *Attorney, Agent, or Firm* — Harness, Dickey & Pierce, P.L.C.

(57) ABSTRACT

A detection device includes an optical device, a suction section adapted to suck the fluid sample in the optical device, a light source adapted to irradiate the optical device with light, a light detection section adapted to detect light emitted from the optical device, and a control section adapted to perform drive control on the suction section. The optical device emits light reflecting the fluid sample to be adsorbed. The control section sets a suction flow velocity of the fluid sample on the optical device to V1 in a first mode including a period of performing detection by the light detection section, sets the suction flow velocity of the fluid sample on the optical device to V2 (V2>V1) in a second mode, and switches between the first mode and the second mode based on a signal from the light detection section.

9 Claims, 13 Drawing Sheets

DETECTION DEVICE

BACKGROUND

1. Technical Field

The present invention relates to a detection device particularly suitable for detection of a trace substance.

2. Related Art

In recent years, as one of sensitive spectroscopic techniques for detecting low-density sample molecules, surface enhanced Raman scattering (SERS) spectroscopy using surface plasmon resonance (SPR), in particular localized surface plasmon resonance (LSPR), has been attracting attention (Japanese Patent No. 3714671, JP-A-2000-356587). The SERS denotes a phenomenon that the Raman scattering light is enhanced $10^2$ through $10^{14}$ times on a metal surface having a structure of providing unevenness in nanometer scale. The sample molecules are irradiated with an excitation light with a single wavelength such as a laser. The light with a scattering wavelength (the Raman scattering light) shifted from the wavelength of the excitation light as much as the molecular vibration energy of the sample molecules is spectroscopically detected to thereby obtain the fingerprint spectrum of the sample molecules. It becomes possible to identify the sample molecules based on the shape of the fingerprint spectrum.

The surface plasmon resonance sensor of this kind is formed by fixing metal fine particles made of, for example, gold or silver on a substrate. The detection device provided with this sensor irradiates the sample molecules adsorbed to the metal nanoparticles of the surface plasmon resonance sensor with light, and then detects the Raman scattering light thus enhanced.

Here, as one of the usages of the surface plasmon resonance sensor, there is cited, for example, monitoring of an environmental pollutant. In order to monitor the pollutant, it is required to detect the pollutant in real time.

However, according to the detection device described above, although it is possible to detect whether or not the sample molecules adsorbed to the metal nanoparticles of the surface plasmon resonance sensor are pollutants, the detection can be performed only once. Therefore, if the presence or absence of the sample molecules in space is detected a number of times in real time, it is not achievable to detect whether or not the sample molecules surely exist at a density equal to or higher than a certain level, or whether or not the density at which the sample molecules exist is surely equal to or lower than a certain level with improved reliability.

SUMMARY

According to some of the aspects of the invention, it is possible to provide a detection device or the like capable of real-time measurement with improved reliability of the inspection.

(1) An aspect of the invention is directed to a detection device including an optical device, a suction section adapted to suck the fluid sample in the optical device, a light source adapted to irradiate the optical device with light, a light detection section adapted to detect light emitted from the optical device, and a control section adapted to perform drive control on the suction section, wherein the optical device emits light reflecting the fluid sample to be adsorbed, and the control section sets a suction flow velocity of the fluid sample on the optical device to V1 in a first mode including a period of performing detection by the light detection section, sets the suction flow velocity of the fluid sample on the optical device to V2 (V2>V1) in a second mode, and switches between the first mode and the second mode based on a signal from the light detection section.

According to this aspect of the invention, since the fluid sample sucked at the flow velocity V1 can be adsorbed to the optical device in the first mode, the first mode can also be referred to as an adsorption mode. If the optical device is irradiated with the light from the light source in the first mode, the light reflecting the fluid sample adsorbed to the optical device is generated. The light detection section is capable of detecting the light from the optical device. In that context, the first mode can also be referred to as an inspection mode in which an inspection is performed. On the other hand, in the second mode, the flow velocity V2 higher than the flow velocity V1 in the first mode (the adsorption mode or the inspection mode) is set. Therefore, in the second mode, it is possible to make the fluid sample adsorbed to the optical device break away therefrom, and the second mode can be referred to as a breakaway mode.

As described above, by performing the first mode and the second mode alternately, the fluid sample once adsorbed to the optical device can be made to break away. In such a manner, it is possible to clean up the optical device after the inspection, and it becomes possible to repeatedly perform a subsequent inspection without leaving the influence of the previous inspection. Therefore, by performing the first and second modes alternately in a repeated manner, the real-time inspection becomes possible. Moreover, since it is possible to clean up the optical device after the inspection, the determination on whether or not the inspection target material exists in the fluid sample at a concentration equal to or higher than a predetermined concentration can be performed with high reliability.

(2) In one aspect of the invention, in the detection device according to the above aspect of the invention, the optical device generates a Raman scattering light of the fluid sample, and the optical detection section detects the Raman scattering light of a material, which can exist in the fluid sample. The Raman scattering light is an example of a signal reflecting the inspection target material, and it is possible to determine whether or not the inspection target material exists in the fluid sample.

(3) In one aspect of the invention, in the detection device according to the above aspect of the invention, the optical device can be provided with a metal nanostructure having projections in a range of 1 through 1000 nm. According to this configuration, an enhanced electric field is formed around the projection of the metal nanostructure, and the signal intensity of the Raman scattering light enhanced by the enhanced electric field becomes stronger.

(4) In one aspect of the invention, in the detection device according to the above aspect of the invention, the suction section includes a negative pressure generation section, and the control section can perform adjustment control on the drive condition of the negative pressure generation section. By performing the adjustment control on the drive condition of the negative pressure generation section, for example, the fluid transport amount per unit time, the flow velocity of the fluid sample on the optical device can be controlled.

(5) In one aspect of the invention, in the detection device according to the above aspect of the invention, the control section can stop driving the negative pressure generation section in the first mode. Some inspection target materials easily break away from the optical device, and the materials break away from the optical device only with, for example, the fluid transport amount per unit time, which is caused by the negative pressure generation section such as a fan, exceeding 0. In such a case, the control section stops driving the negative pressure generation section in the first mode. If the second mode is performed prior to the first mode, the flow velocity of the fluid sample on the optical device can be assured using the flow amount and the inertia in the second mode. Thus, the material in the fluid sample can be adsorbed to the optical device even if the drive of the negative pressure generation section is stopped.

(6) In one aspect of the invention, in the detection device according to the above aspect of the invention, the control section can perform switching from the first mode to the second mode in response to a level of the signal from the light detection section exceeding a first threshold level. The material in the fluid sample sucked therein is adsorbed to the optical device in the first mode, and the signal intensity from the light detection section increases in conjunction therewith. The inspection of presence or absence of the inspection target material can be performed before the signal level reaches the first threshold level. Therefore, if the level of the signal from the light detection section exceeds the first threshold level, switching from the first mode to the second mode is allowed. In the second mode, by making the material once adsorbed break away, the optical device can be cleaned up prior to the subsequent inspection.

(7) In one aspect of the invention, in the detection device according to the above aspect of the invention, the control section can perform switching from the second mode to the first mode in response to the level of the signal from the light detection section falling below a second threshold level lower than the first threshold level. The purpose of the execution of the second mode is to make the fluid sample break away from the optical device. If the level of the signal from the light detection section is equal to or lower than the second threshold level, it is possible to determine that the breakaway is sufficiently performed, and to end the second mode to make a transition to the first mode.

(8) In one aspect of the invention, the detection device according to the above aspect of the invention further includes a supply section adapted to supply the optical device with a reference sample in the first mode, the light detection section detects a signal reflecting the reference sample at a wavelength different from that of the inspection target material, which can exist in the fluid sample, and the control section can perform switching from the first mode to the second mode in response to a level of the signal reflecting the reference sample exceeding a third threshold level despite the level of the signal reflecting the inspection target material is lower than the first threshold level. It is arranged that even in the case in which the inspection target material does not exist or only infinitesimal quantity thereof exists in normal cases like trinitrotoluene (TNT) molecules, transition from the first mode to the second mode is possible by performing the control based on the comparison between the signal reflecting the reference sample and the third threshold level in combination.

(9) In one aspect of the invention, in the detection device according to the above aspect of the invention, the control section can perform switching from the second mode to the first mode in response to a level of the signal reflecting the reference sample falling below a fourth threshold level lower than the third threshold level despite the level of the signal reflecting the inspection target material is higher than the second threshold level. Similarly to the above, it is arranged that even in the case in which the inspection target material does not exist or only infinitesimal quantity thereof exists in normal cases like TNT molecules, transition from the second mode to the first mode is possible by performing the control based on the comparison between the signal reflecting the reference sample and the fourth threshold level in combination.

(10) In one aspect of the invention, in the detection device according to the above aspect of the invention, the supply section can supply a constant amount of the reference sample during the first mode. The total amount of the reference sample supplied from the supply section can be obtained by, for example, (vapor pressure)×(time), and by making the total amount constant, even in the case in which the concentration of the inspection target material is too low to detect the inspection target material, it becomes possible to set the period of the first mode to be roughly constant to perform the switching to the second mode.

(11) In one aspect of the invention, in the detection device according to the above aspect of the invention, the reference sample can be set to a molecule including at least one of a hetero ring, a benzene ring, a COOH group, an OH group, a CHO group, an S atom, and an N atom. These groups and atoms can adhere or be bonded to metals with relative ease, and the molecules can surely be detected. Therefore, the molecules can be made to function as the reference sample.

(12) In one aspect of the invention, in the detection device according to the above aspect of the invention, the control section can perform switching in order of the second mode, the first mode, and the second mode. As described above, due to the second mode performed prior to the first mode, the optical device is cleaned up prior to the detection to thereby improve the detection accuracy, and due to the second mode performed after the first mode, it is possible to clean up the optical device prior to the subsequent detection. Therefore, an advantage to the real-time detection can be obtained.

BRIEF DESCRIPTION OF THE DRAWINGS

The invention will be described with reference to the accompanying drawings, wherein like numbers reference like elements.

DESCRIPTION OF AN EXEMPLARY EMBODIMENT

Hereinafter, a preferred embodiment of the invention will be described in detail. It should be noted that the present embodiments explained below do not unreasonably limit the content of the invention as set forth in the appended claims, and all of the constituents set forth in the present embodiments are not necessarily essential as means of the invention for solving the problems.

1. Basic Configuration of Detection Device

Figure 1:
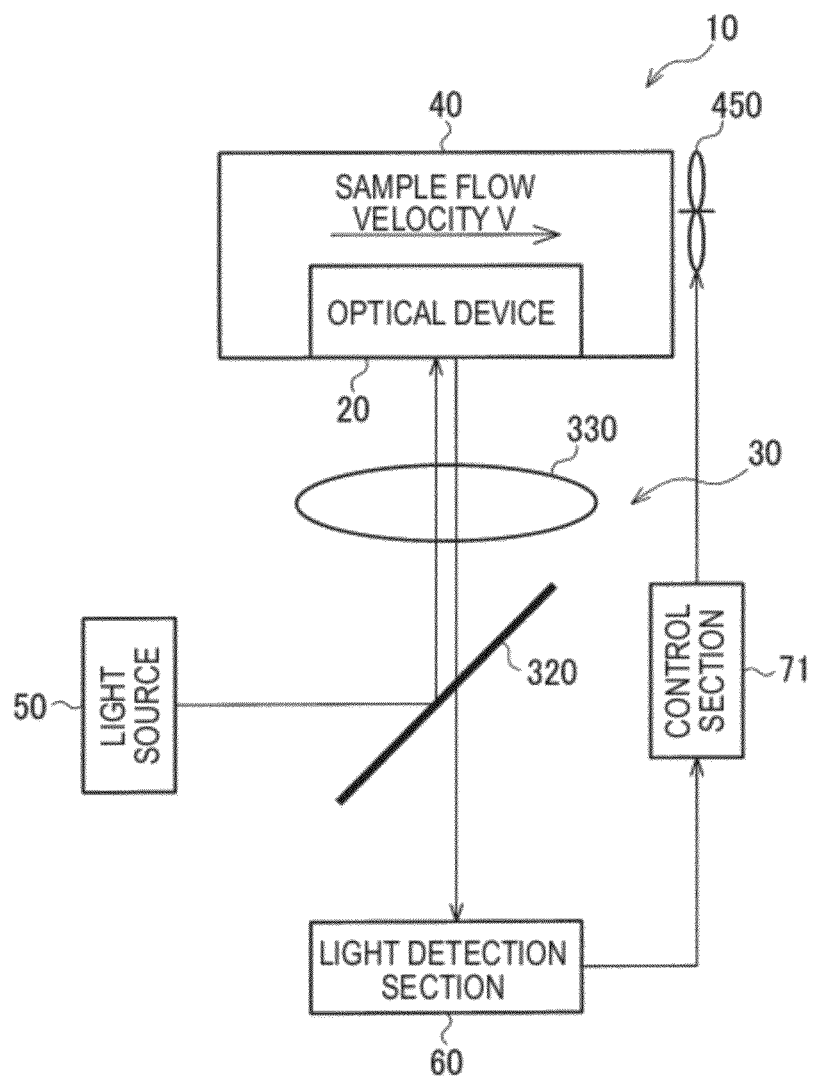
FIG. 1 is a diagram showing a rough outline of a detection device according to an embodiment of the invention.

FIG. 1 shows a configuration example of a detection device according to an embodiment of the invention. In FIG. 1, the detection device 10 has an optical device 20, a suction section 40, a light source 50, a light detection section 60, and a control section 71. It is possible to dispose an optical system 30 between the optical device 20 and one of the light source 50, the light detection section 60, and both of the light source 50 and the light detection section 60.

The optical device 20 is irradiated with the light from the light source 50 and emits light reflecting a fluid sample adhered thereto in response to the irradiation of the light. In the present embodiment, the fluid sample is, for example, air, and the inspection target material can be set to specific gas molecules (sample molecules) in the air, but is not limited thereto.

The suction section 40 sucks the fluid sample in the optical device 20. The light source 50 irradiates the optical device 20 with light via, for example, a half mirror 320 and an objective lens 330 constituting, for example, the optical system 30. The light detection section 60 detects the light reflecting the fluid sample adsorbed to the optical device 20 via the half mirror 320 and the objective lens 330.

Figure 2:
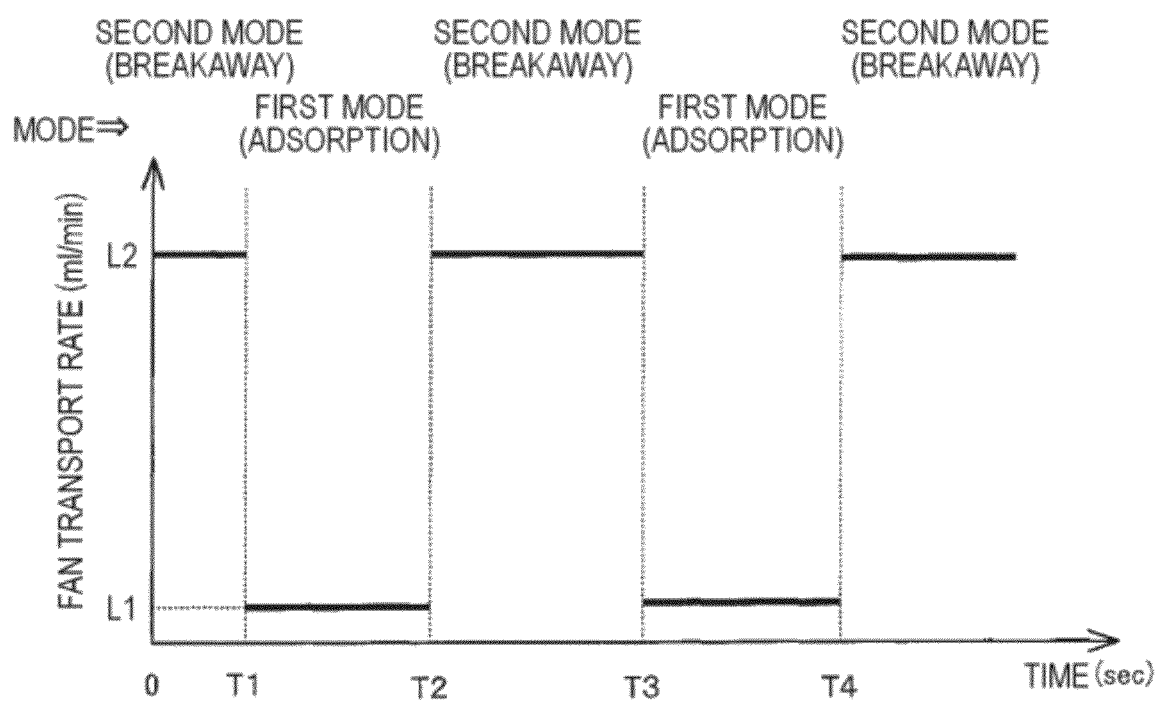
FIG. 2 is a time chart showing a first mode and a second mode.

The control section 71 performs switching control between first and second modes shown in FIG. 2 based on the signal from the light detection section 60. Here, the first mode includes the period in which the light detection section 60 performs the detection. The control section 71 performs drive control of a negative pressure generation section such as a fan 450 provided to the suction section 40 so as to set the suction flow velocity V of the fluid sample on the optical device 20 to V1 (m/min) in the first mode, and set the suction flow velocity to V2 (V2>V1) in the second mode. The negative pressure generation section is not limited to the fan, but is only required to be what can generate a negative pressure in the suction section 40 to thereby suck the fluid sample such as a pump including a tube pump, a diaphragm pump, and so on. As shown in FIG. 2, the fan 450 provides the fluid transport rate (the flow rate) of L1 (ml/min) in the first mode, and the fluid transport rate (the flow rate) of L2 (ml/min) in the second mode, and fulfills L2>L1. The control of the suction speed can be performed on the fan 450 as a target as described above, or can be achieved by varying the area of an opening of a valve or a shutter. It is sufficient that the suction speed of the fluid sample on the optical device 20 can be varied as a result of the control.

In the present embodiment, since the fluid sample sucked at the flow velocity V1 can be adsorbed to the optical device 20 in the first mode, the first mode can also be referred to as an adsorption mode. If the optical device 20 is irradiated with the light from the light source 30 in the first mode, the light reflecting the fluid sample adsorbed to the optical device 20 is generated. The light detection section 60 is capable of detecting the light from the optical device 20. In that context, the first mode can also be referred to as an inspection mode in which an inspection is performed.

On the other hand, in the second mode, the flow velocity V2 higher than the flow velocity V1 in the first mode (the adsorption mode or the inspection mode) is set. Therefore, in the second mode, it is possible to make the fluid sample adsorbed to the optical device 20 break away therefrom, and the second mode can be referred to as a breakaway mode.

As described above, by performing the first mode and the second mode alternately, the fluid sample once adsorbed to the optical device 20 can be made to break away. In such a manner, it is possible to clean up the optical device 20 after the inspection, and it becomes possible to repeatedly perform a subsequent inspection without leaving the influence of the previous inspection. For example, as shown in FIG. 2, by performing the second mode prior to the first mode, it is possible to perform inspection with the fluid sample adsorbed to the optical device 20 kept in a fresh state. By performing the first and second modes alternately in a repeated manner, the real-time inspection becomes possible.

Here, the flow velocities V1, V2 in the first and second modes are each a flow velocity of the fluid sample on the optical device 20, and the fan 450 is driven so that the flow velocities V1, V2 can be obtained. On this occasion, in the case of performing the first and second modes alternately in a repeated manner, it is also possible to stop the drive of the fan 450 with the first mode (L1=0). In this case, the flow velocity V1 (V1≠0) of the fluid sample on the optical device 20 can be assured using the amount of flow and the inertia in the second mode.

Figure 3:
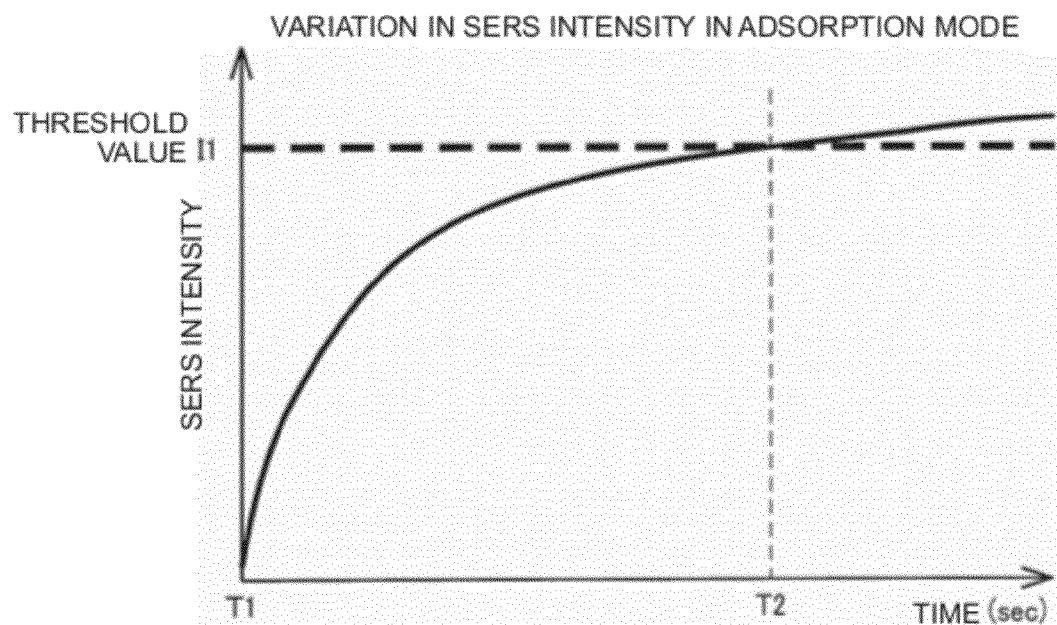
FIG. 3 is a characteristic diagram showing an intensity variation of a detection signal in the first mode.

The switching between the first and second modes can be performed based on the output of the light detection section 60. This is because the light detection signal changes due to the adsorption and breakaway of the fluid sample between the first and second modes. FIG. 3 shows, for example, a variation in the SERS intensity of the sample molecules as the inspection target in the fluid sample as the output of the light detection section 60 in the first mode (the adsorption mode or the inspection mode) in the period from the time T1 to the time T2. In the first mode started at the time T1, the amount of the sample molecules adsorbed to the optical device 20 increases. Therefore, the SERS intensity increases in the first mode. Therefore, it is possible to end the first mode at the time T2 at which the SERS intensity exceeds a first threshold level I1 shown in FIG. 3.

Figure 4:
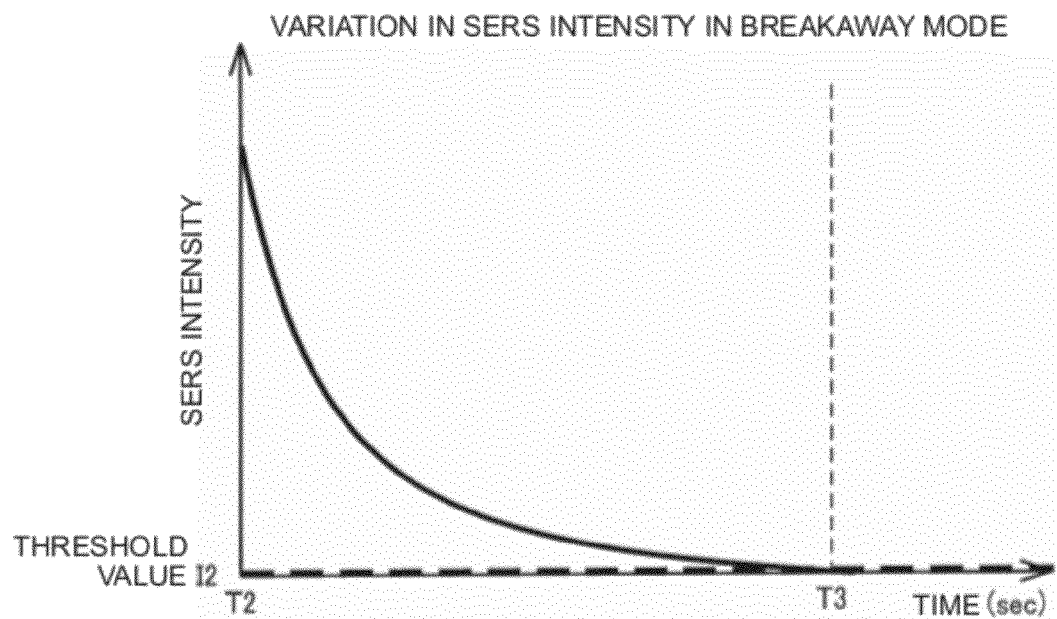
FIG. 4 is a characteristic diagram showing an intensity variation of the detection signal in the second mode.

FIG. 4 similarly shows the variation in the SERS intensity of the sample molecules as the inspection target in the fluid sample as the output of the light detection section 60 in the second mode (the breakaway mode). In the second mode started at the time T2, the amount of the sample molecules breaking away from the optical device 20 increases. Therefore, the SERS intensity decreases in the second mode. Therefore, it is possible to end the second mode at the time T3 at which the SERS intensity falls below a second threshold level I2 shown in FIG. 4.

It should be noted that the SERS intensity is a value based on the number of photons received by a light receiving element of the light detection section 60 shown in FIG. 1. The first threshold level I1 corresponds to the number of photons of, for example, 200, and the second threshold level I2 can be set to the number of photons of, for example, 10.

2. One Example of Principle and Structure of Light Detection

Figure 5A:
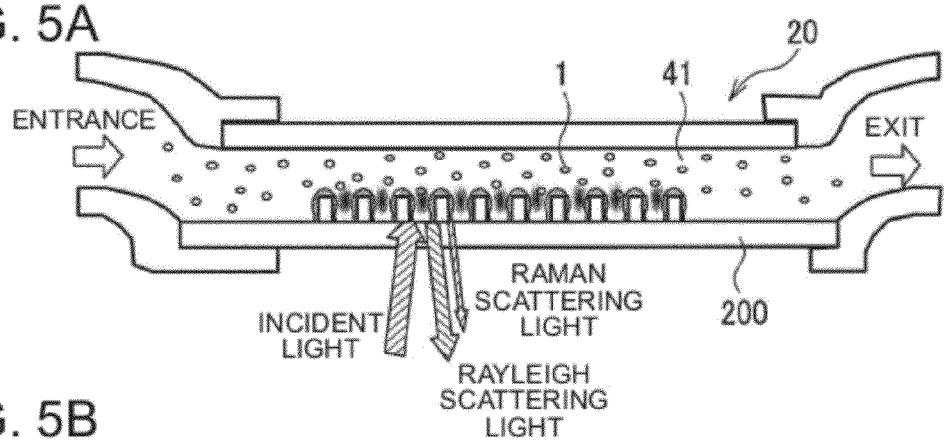
FIG. 5A is an enlarged cross-sectional view of a suction section and an optical device.
Figure 5B:
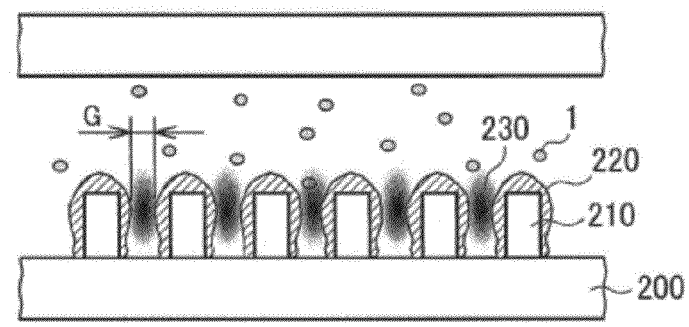
FIGS. 5B and 5C are cross-sectional view and a plan view showing formation of an enhanced electric field in an optical device.
Figure 5C:
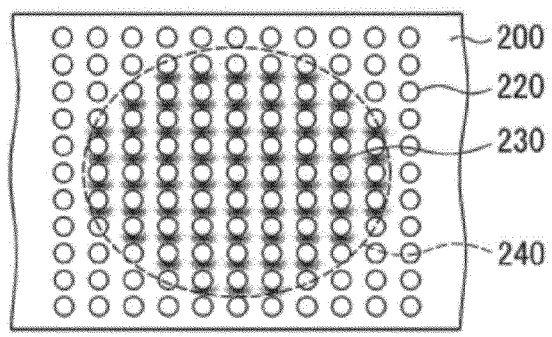

Explanatory diagrams of the detection principle of the Raman scattering light as one example of the light detection principle reflecting the fluid sample will be shown using FIGS. 5A through 5C. As shown in FIG. 5A, the sample molecules 1 as the inspection target adsorbed to the optical device 20 are irradiated with the incident light (vibration frequency ν). In general, a most part of the incident light is scattered as the Rayleigh scattering light, and the vibration frequency ν or the wavelength of the Rayleigh scattering light is not varied with respect to the incident light. A part of the incident light is scattered as the Raman scattering light, and the vibration frequency (ν−ν' and ν+ν') or the wavelength of the Raman scattering light reflects the vibration frequency ν' (molecular vibration) of the sample molecules 1. In other words, the Raman scattering light is light reflecting the sample molecules 1 as the inspection target. Although the part of the incident light excites the sample molecules 1 to thereby lose the energy, in some cases, the vibration energy of the sample molecules 1 is added to the vibration energy or the light energy of the Raman scattering light. Such a shift (ν') in the vibration frequency as described above is referred to as a Raman shift.

FIG. 5B is an enlarged view of the optical device 20 shown in FIGS. 1 and 5A. In the case in which the incident light enters the flat surface of the substrate 200 as shown in FIG. 5A, a material transparent to the incident light is used for the substrate 200. The optical device 20 has a plurality of projections 210 made of a dielectric material as a first structure on the substrate 200. In the present embodiment, a resist is formed on the substrate 200 made of quartz, crystal, glass such as borosilicate glass, silicon, or the like as the dielectric material transparent to the incident light, and then the resist is patterned using, for example, a deep ultraviolet (DUV) photolithography process. By etching the substrate 200 using the resist thus patterned, the plurality of projections 210 are arranged, for example, in a two-dimensional manner as shown in FIG. 5C. It should be noted that the substrate 200 and the projections 210 can also be made of respective materials different from each other.

As a second structure on the plurality of projections 210, the plurality of projections 210 is provided with metal nanoparticles (metal fine particles) 220 made of, for example, Au or Ag formed by, for example, evaporation or sputtering. As a result, the optical device 20 can be provided with a metal nanostructure having the projections in a range of 1 through 1000 nm. The metal nanostructure having the projections in a range of 1 through 1000 nm can be formed by a method of fixing the metal fine particles of the above size on the substrate by evaporation, sputtering, and so on, or a method of forming a metal film having an island structure on the substrate besides the method of processing the upper surface of the substrate 200 so as to have the projection structure (with the substrate material) of the above size.

As shown in FIGS. 5B and 5C, in the area 240 where the incident light enters the metal nanoparticles 220 arranged in a two-dimensional pattern, an enhanced electric field 230 is formed in the gap G between the metal nanoparticles 220 adjacent to each other. In particular, in the case of irradiating the metal nanoparticles 220 smaller than the wavelength of the incident light with the incident light, the electric field of the incident light affects the free electrons existing on the surface of the metal nanoparticles 220 to cause resonance. Thus, the electric dipoles due to the free electrons are excited in the metal nanoparticles 220, and the enhanced electric field 230 stronger than the electric field of the incident light is formed. This phenomenon is also called localized surface plasmon resonance (LSPR). This phenomenon is unique to the electric conductor having the projections in a range of 1 through 1000 nm smaller than the wavelength of the incident light such as metal nanoparticles 220.

In FIGS. 5A through 5C, when irradiating the optical device 20 with the incident light, the surface enhanced Raman scattering (SERS) occurs. Specifically, if the sample molecules 1 get into the enhanced electric field 230, the Raman scattering light due to the sample molecules 1 is enhanced by the enhanced electric field 230, and the signal intensity of the Raman scattering light increases. In such a surface enhanced Raman scattering, the detection sensitivity can be enhanced even with a minute amount of sample molecules 1.

The phenomenon called "adsorption" of the sample molecules 1 described below is a phenomenon in which the number (partial pressure) of colliding molecules, namely the sample molecules 1 colliding with the metal nanoparticles 220, is predominant, and includes one or both of physical adsorption and chemical adsorption. The term "breakaway" means that the adsorption is released due to an external force. The adsorption energy depends on the kinetic energy of the sample molecules 1, and causes the "adsorption" phenomenon due to the collision if the adsorption energy exceeds a certain value. The adsorption does not require any external force. In contrast, the breakaway requires an external force. Further, the suction of the fluid sample to the optical device 20 is to cause a suction flow in a flow channel having the optical device 20 disposed in the inside thereof in other words, and to make the fluid sample have contact with the optical device 20.

3. Specific Configuration of Detection Device

Figure 6:
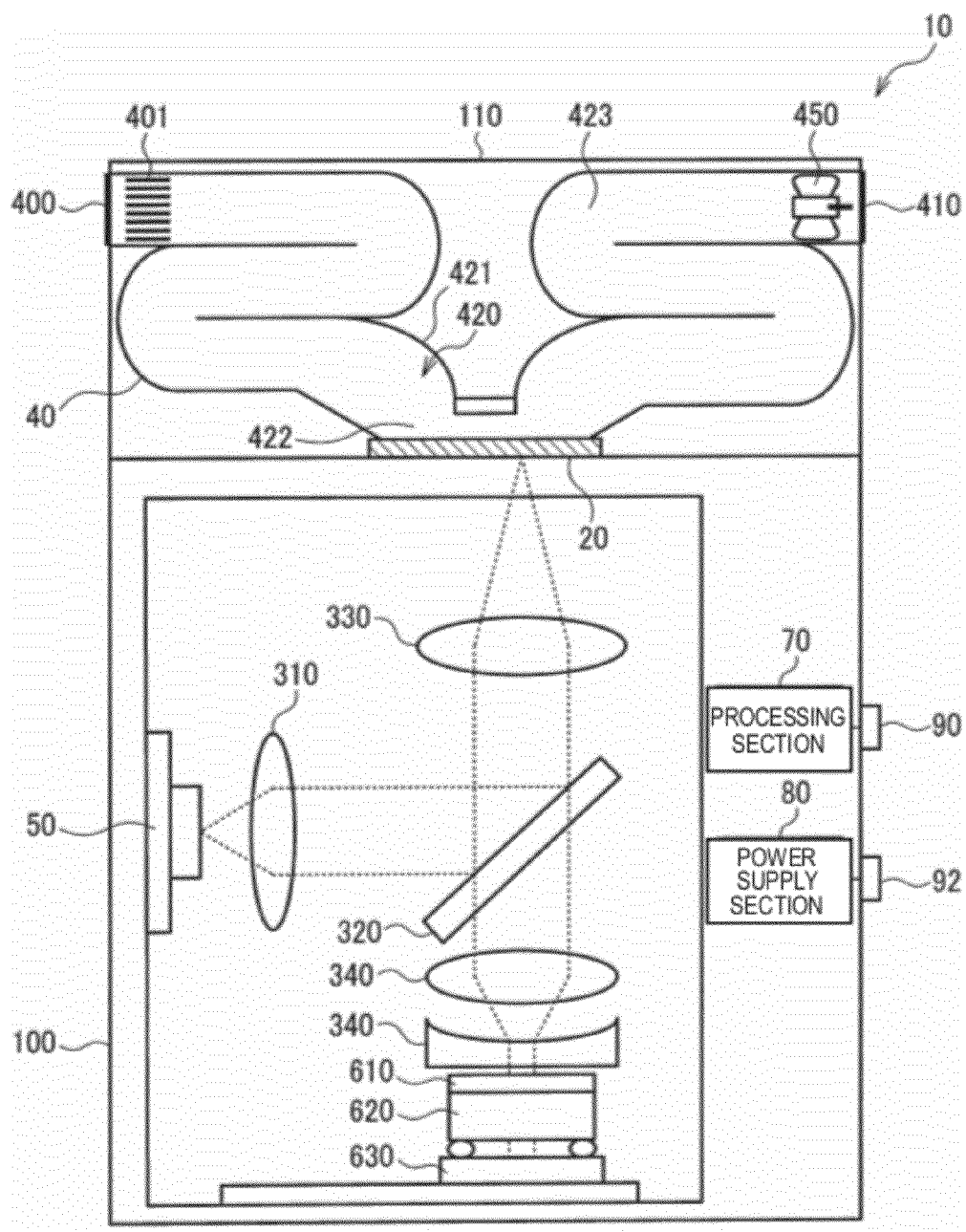
FIG. 6 is a block diagram showing an overall outline of an inspection device.

FIG. 6 shows a specific configuration example of the detection device according to the present embodiment. The detection device 10 shown in FIG. 6 also has the optical device 20, the optical system 30, the suction section 40, the light source 50, and the light detection section 60 (610, 620, and 630 in FIG. 6) shown in FIG. 1, and a processing section 70 including the control section 71 shown in FIG. 1.

In FIG. 6, the light source 50 is a laser, and a vertical cavity surface emitting laser can preferably be used therefore from the viewpoint of miniaturization, but the light source 50 is not limited thereto.

The light from the light source 50 is collimated by a collimator lens 310 constituting the optical system 30. It is also possible to dispose a polarization control element on the downstream of the collimator lens 310 to thereby convert the light into a linearly polarized light. It should be noted that if the surface emission laser is adopted as the light source 50, and thus the light with the linear polarization light can be emitted, the polarization control element can be eliminated.

The light collimated by the collimator lens 310 is guided toward the optical device 20 by the half mirror (the dichroic mirror) 320, then converged by the objective lens 330, and then enters the optical device 20. The optical device 20 is provided with the metal nanoparticles 220 shown in FIGS. 5A through 5C. The optical device 20 radiates, for example, the Rayleigh scattering light and the Raman scattering light due to the surface enhanced Raman scattering. The Rayleigh scattering light and the Raman scattering light from the optical device 20 pass through the objective lens 330, and is then guided toward the light detection section 60 by the half mirror 320.

The Rayleigh scattering light and the Raman scattering light from the optical device 20 are converged by collecting lenses 340, and is then input to the light detection section 60. In the light detection section 60, firstly, the lights reach an optical filter 610. The optical filter 610 (e.g., a notch filter) takes out the Raman scattering light. The Raman scattering light is further received by a light receiving element 630 via a spectroscope 620. The spectroscope 620 is formed of, for example, an etalon using the Fabry-Perot resonance, and can be made to have a variable pass frequency band. The wavelength of the light passing through the spectroscope 620 can be controlled (selected) by the control section 71. The Raman spectrum unique to the sample molecules 1 can be obtained by the light receiving element 630, and the Raman spectrum thus obtained and the data held previously are compared with each other for matching to thereby make it possible to identify the sample molecules 1.

The suction section 40 has an induction section 420 disposed between a suction port 400 and a discharge port 410. The fluid sample including the sample molecules 1 is introduced from the suction port 400 (carry-in entrance) into the inside of the induction section 420, and then discharged outside the induction section 420 from the discharge port 410. A dust removal filter 401 can be disposed on the suction port 400 side. In FIG. 6, the detection device 10 has the fan 450 in the vicinity of the discharge port 410, and when activating the fan 450, the pressure (atmospheric pressure) inside a suction channel 421 of the induction section 420, a flow channel 422 in the vicinity of the optical device 20, and a discharge channel 423 falls. Thus, the fluid sample is sucked in the induction section 420 together with the sample molecules 1. The fluid sample passes through the suction channel 421, and is then discharged from the discharge channel 423 via the channel 422 in the vicinity of the optical device 20. On this occasion, some of the sample molecules 1 are adsorbed to the surface (electric conductor) of the optical device 20.

The sample molecules 1 as the inspection target material can be assumed to be rare molecules of, for example, narcotic drugs, alcohol, and residual pesticides, pathogens such as viruses, and so on, and the present embodiment is particularly suitable for detecting such sample molecules 1 in real time.

The detection device 10 has a housing 100, and has, for example, the optical system 30, the light source 50, the light detection section 60, and the processing section 70 inside the housing 100. Further, the detection device 10 can include a power supply section 80, a communication connection section 90, and a power supply connection section 92 inside the housing 100. The power supply section 80 supplies the light source 50, the light detection section 60, the processing section 70, the fan 450, and so on with the power from the power supply connection section 92. The power supply section 80 can be formed of, for example, a secondary battery, and can also be formed of a primary battery, an AC adapter, and so on. The communication connection section 90 is connected to the processing section 70, and transmits data, control signals, and so on to the processing section 70. The detection device 10 has a cover 110, and the cover 110 is capable of housing the optical device 20 and so on.

In the example shown in FIG. 6, the processing section 70 can send commands to the light detection section 60, the fan 450, and so on except the light source 50 shown in FIG. 6. Further, the processing section 70 is capable of performing a spectroscopic analysis using the Raman spectrum, and the processing section 70 is also capable of identifying the sample molecules 1 as the target object. It should be noted that the processing section 70 can transmit the detection result using the Raman scattering light, the spectroscopic analysis result using the Raman spectrum, and so on to, for example, external equipment (not shown) connected to the communication connection section 90.

Figure 7:
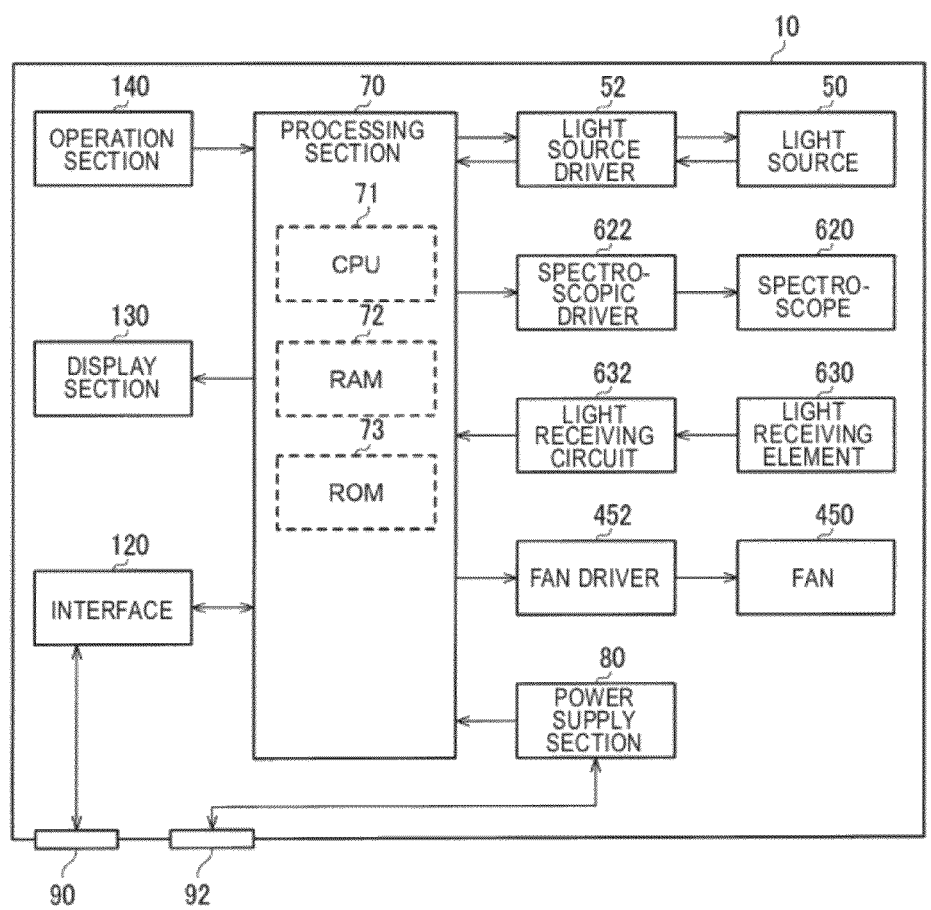
FIG. 7 is a block diagram of a control system of the inspection device.

FIG. 7 is a block diagram of a control system of the detection device 10 shown in FIG. 6. As shown in FIG. 7, the detection device 10 can further include an interface 120, a display section 130, an operation section 140, and so on. Further, as shown in FIG. 7, the processing section 70 shown in FIG. 6 can include a central processing unit (CPU) 71 as the control section, a random access memory (RAM) 72, a read only memory (ROM) 73, and so on. Further, the detection section 10 can include, for example, a light source driver 52, a spectroscopic driver 622, alight receiving circuit 632, and a fan driver 452.

4. Switching Between First Mode and Second Mode 4.1. First Experimental Example

Figure 8:
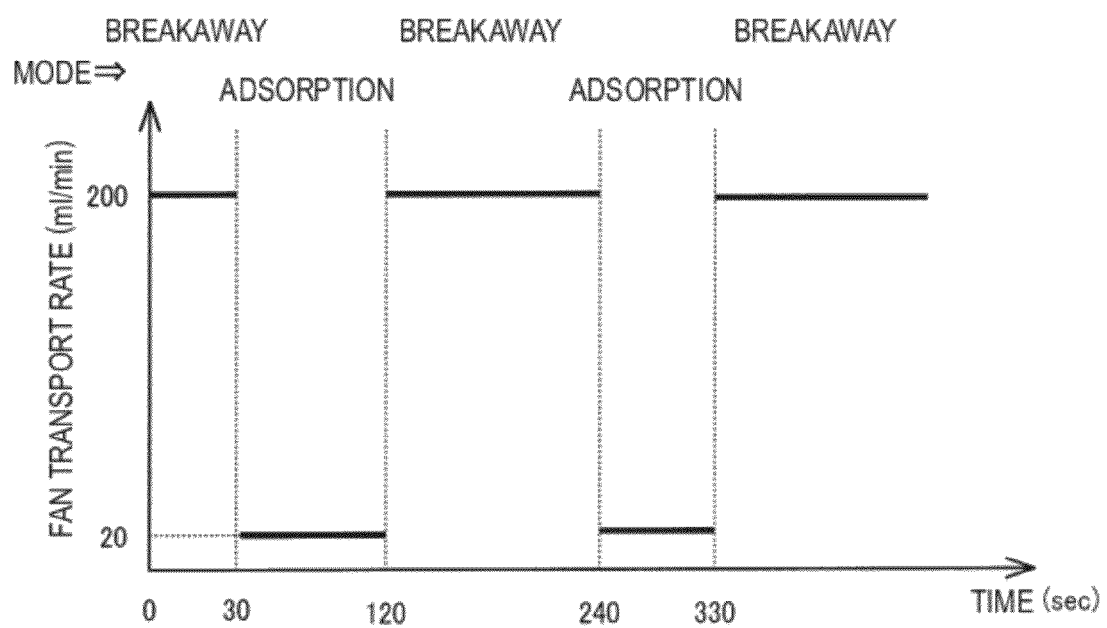
FIG. 8 is a time chart of the first and second modes in a first experimental example.
Figure 9:
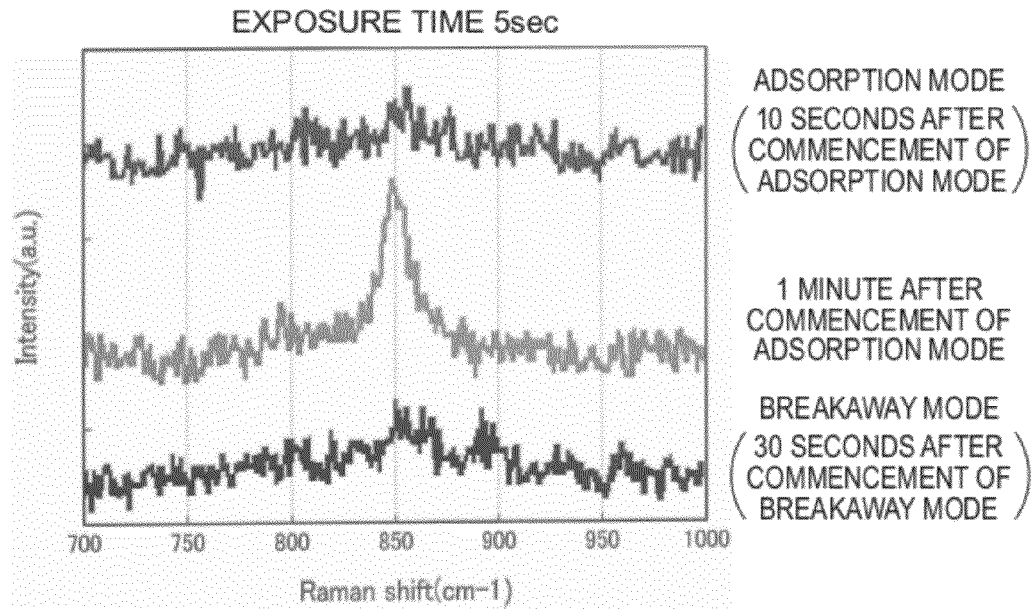
FIG. 9 is a characteristic diagram showing a measurement result in the first experimental example.

FIG. 9 shows a result of actual measurement using lactic acid gas molecules as the sample molecules 1 as the inspection target material performed in accordance with the time chart of the first mode (the adsorption mode) and the second mode (the breakaway mode) shown in FIG. 8. As the light source 50 shown in FIG. 6, a He—Ne laser with an excitation wavelength of 632.8 nm and intensity of 0.2 mW is used. The measurement exposure time in the light detection section 60 shown in FIG. 6 is set to 5 seconds, and the material of the optical device 20 shown in FIG. 6 is Ag. The fluid transport rate L1 of the fan 450 in the first mode (the adsorption mode) is set to 20 ml/min, and the fluid transport rate L2 of the fan 450 in the second mode (the breakaway mode) is set to 200 ml/min.

As shown in FIG. 8, the experiment starts with the breakaway mode for 30 seconds. The mode is switched to the adsorption mode of L1: 20 ml/min, 30 seconds later. FIG. 9 shows the SERS spectrum measured immediately after switching the mode.

Here, the lateral axis of FIG. 9 represents the Raman shift ($cm^{-1}$), and the vertical axis represents the spectral intensity. In FIG. 9, the peak ($vC$—$CO_2^-$) of the lactic acid in the vicinity of 855 $cm^{-1}$ is still inconspicuous 10 seconds after the commencement of the adsorption mode. By performing the SERS measurement setting the time 60 seconds after the commencement of the adsorption mode to the measurement mode, as shown in FIG. 9, it can be confirmed that the peak of the lactic acid in the vicinity of 855 $cm^{-1}$ clearly becomes conspicuous. This proves that the adsorption has been advanced.

Subsequently, the mode is switched to the breakaway mode of L2: 200 ml/min, the breakaway is promoted. In the spectrum measured 30 seconds after the commencement of the breakaway mode, the conspicuous peak of the lactic acid has already been attenuated dramatically. It should be noted that the time described here is nothing more than an example, and needs to appropriately be changed with the material of the optical device 20 and the sample molecules 1.

In the experimental example shown in FIG. 8, although the initial breakaway mode is set to 30 seconds, the subsequent adsorption mode is set to 90 seconds, and the further breakaway mode is set to 120 seconds, in reality, as shown in FIGS. 2 through 4, the mode switching is performed by comparing the SERS intensity with the first threshold level I1 and the second threshold level I2.

4.2. Second Experimental Example

Figure 10:
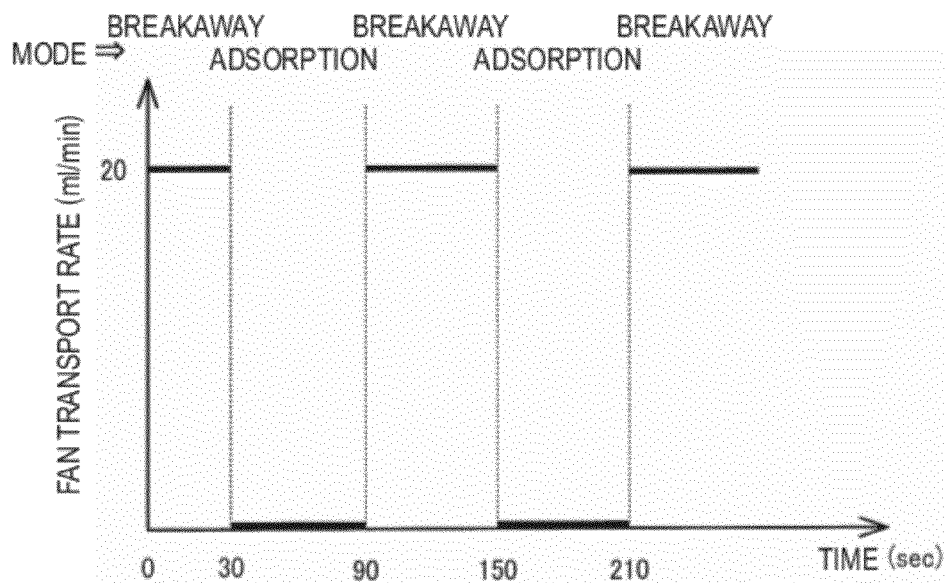
FIG. 10 is a time chart of the first and second modes in a second experimental example.

In the same device as in the first experimental example, isopropyl alcohol (IPA) molecules are used as the sample molecules 1 as the inspection target material, and the measurement is performed setting the measurement exposure time to 10 seconds. In the second experimental example, as shown in FIG. 10, the fluid transport rate L1 of the fan 450 in the first mode (the adsorption mode) is set to 0 ml/min, and the fluid transport rate L2 of the fan 450 in the second mode (the breakaway mode) is set to 20 ml/min. The fluid transport rates L1, L2 in the second experimental example are set lower than the respective fluid transport rates L1, L2 in the first experimental example.

The reason therefor is as follows. The IPA molecules have weak adsorption force to the optical device 20 than that of the lactic acid molecules. The molecules with weak adsorption force such as the IPA molecules often fail to be detected since the breakaway is promoted even at the flow rate of L1>0, and it is preferable to set L1=0 in the adsorption mode. As described above, it is possible to assure the flow velocity V1 (V1≠0) of the sample on the optical device 20 by using the amount of flow and the inertia in the breakaway mode performed prior to the adsorption mode to thereby adsorb the sample molecules 1.

Figure 11:
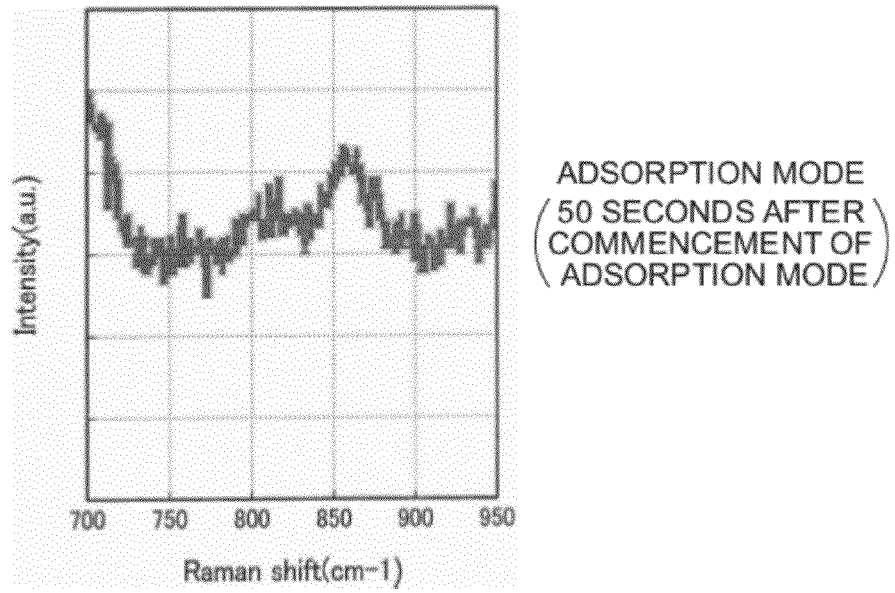
FIG. 11 is a characteristic diagram for testing sample molecules breaking away at a fluid transport rate of 20 ml/min in the second experimental example.

In fact, in the case of the IPA molecules showing the peak in the vicinity of 820 cm$^{-1}$, the breakaway can be observed even in the case in which the fluid transport rate of the fan 450 is 20 ml/min as shown in FIG. 11. Therefore, in the second experimental example, the fluid transport rate L2 of the fan 450 in the second mode (the breakaway mode) is set to 20 ml/min, and the fluid transport rate L1 of the fan 450 in the first mode (the adsorption mode) is set to 0 ml/min.

Figure 12:
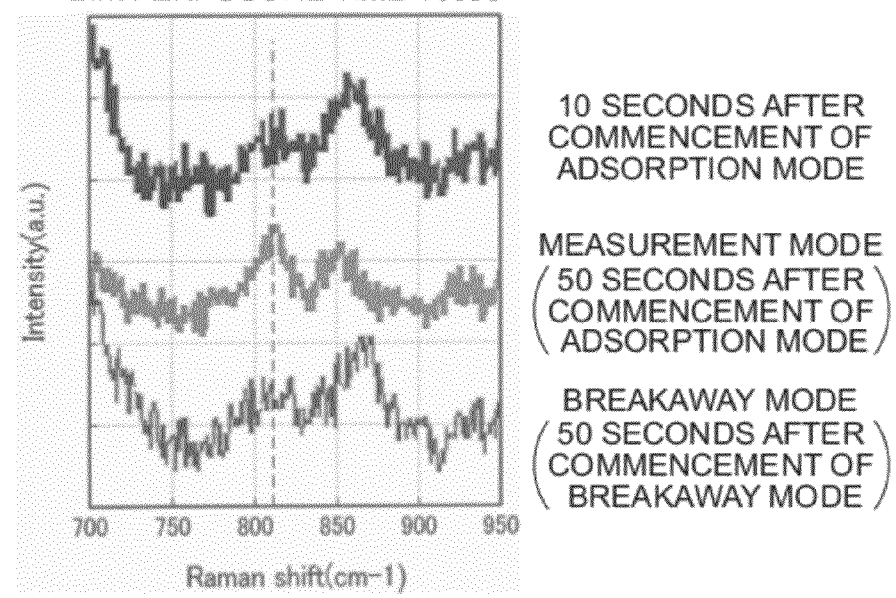
FIG. 12 is a characteristic diagram showing a measurement result in the second experimental example.

FIG. 12 shows the measurement result in the second experimental example. As shown in FIG. 12, the SERS intensity of the IPA molecules showing the peak in the vicinity of 820 cm$^{-1}$ is high 10 seconds after commencement of the adsorption mode setting the fluid transport rate L2 of the fan 450 to 0 ml/min, and even in the measurement mode started 50 seconds after the commencement of the adsorption mode, the peak intensity of the IPA molecules can be detected. In contrast, the breakaway mode shown in FIG. 12 is performed with the fluid transport rate L2 of the fan 450 set to 20 ml/min, and the SERS intensity of the IPA molecules 50 seconds after the commencement of the breakaway mode is in a low level similar to the case shown in FIG. 11.

5. Modified Example Using Reference Molecules in Combination

5.1. Overall Structure

It is assumed that TNT molecules as component molecules of an explosive are detected as the inspection target material in, for example, a port or a harbor. In normal cases, the TNT molecules do not exist in the air. Therefore, if the detection along the method of the embodiment described above taking the TNT molecules as the sample molecules, it takes eternity to end the adsorption mode. This is because there is high probability that in normal cases the SERS intensity of the TNT molecules does not exceed the first threshold level I1 even if the adsorption mode is set. On this occasion, the breakaway mode is not started. Therefore, the surface of the optical device 20 is contaminated with other molecules, and the adsorption sites are saturated, and it becomes unachievable to adsorb the TNT molecules as the inspection target material. Therefore, the reliability of the determination that no sample molecule 1 surely exists or that an infinitesimal quantity of sample molecules 1 exists is degraded. According to the present embodiment, it becomes possible to repeatedly make transition to the breakaway mode even in the normal case where TNT molecules do not exist, or only an infinitesimal quantity of which exists.

Figure 13:
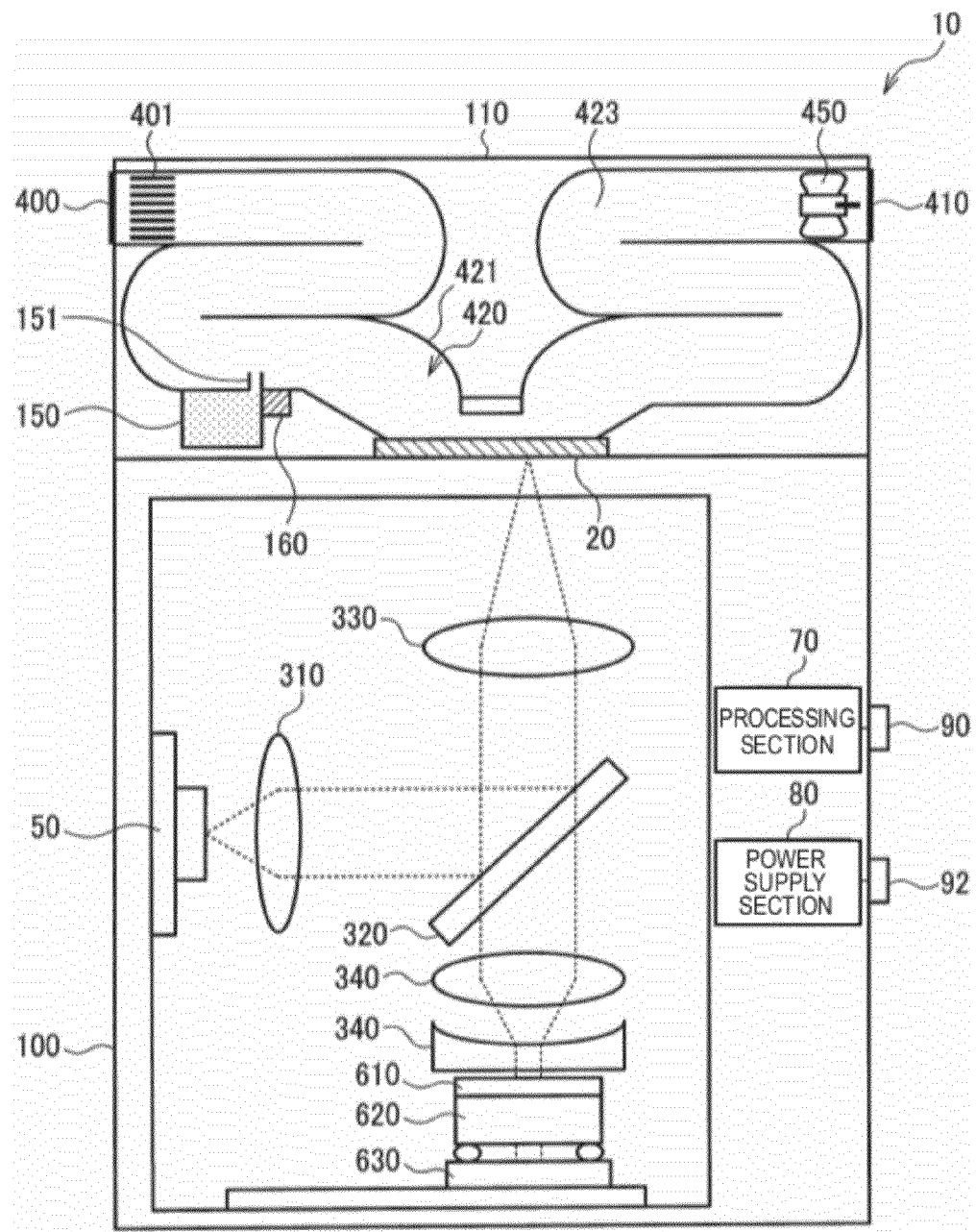
FIG. 13 is a block diagram of a detection device according to an embodiment using detection of reference molecules (a reference sample) in combination.

FIG. 13 is a block diagram of the present embodiment of including the reference molecules in addition to the sample molecules in the fluid sample, and switching between the first and second modes based on the detection signals of the sample molecules and the reference molecules. In FIG. 13, a reference molecule storage chamber 150 is disposed on the upstream side of the optical device 20 of the suction section 40 in addition to the configuration shown in FIG. 6. The reference molecule storage chamber 150 has an ejection port 151 for ejecting the reference molecules to the induction section 420. The reference molecule storage chamber 150 is provided with an ejection drive section 160. The ejection drive section 160 ejects a predetermined amount of reference molecules to the induction section 420 via the ejection port 151 continuously for a predetermined period of time at predetermined timings. The reference molecule storage chamber 150, the ejection port 151, and the ejection drive section 160 constitute an example of a reference molecule supply section. Here, the reference molecules need to fulfill the requirement of being capable of detecting the Raman scattering light at a wavelength different from that of the sample molecules as the inspection target material.

The spectroscope 620 shown in FIG. 13 is a device from which the light having a variable wavelength band is taken out such as an etalon, or a device from which a plurality of lights having different wavelength can simultaneously be taken out such as a diffraction grating, and the Raman scattering lights of the sample molecules and the reference molecules are taken out. The light receiving element 630 shown in FIG. 13 is capable of detecting the SERS intensity of each of the sample molecules and the reference molecules.

Figure 14:
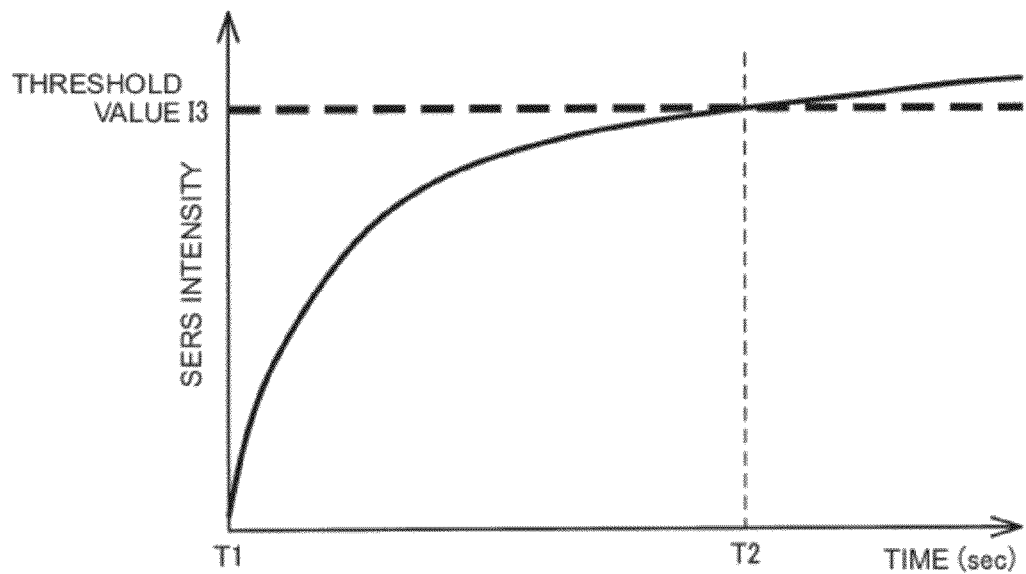
FIG. 14 is a characteristic diagram showing a variation in the spectral intensity of the reference molecules in the first mode.

FIG. 14 shows the variation in the SERS intensity of the reference molecules as the output of the light detection section 60 during the period in which the reference molecules are continuously supplied from the reference molecule storage chamber 150. The amount of the reference molecules adsorbed to the optical device 20 increases with the elapsed time from the commencement of the supply of the reference molecules. Therefore, if the supply of the reference molecules is performed in the first mode (the adsorption mode), the SERS intensity of the reference molecules increases. Therefore, it is possible to end the first mode at the time T2 at which the SERS intensity exceeds a third threshold level I3 shown in FIG. 14. It is possible to stop the supply of the reference molecules when the supply of a constant amount of the reference molecules is completed during the first mode, or when the first mode is terminated.

Figure 15:
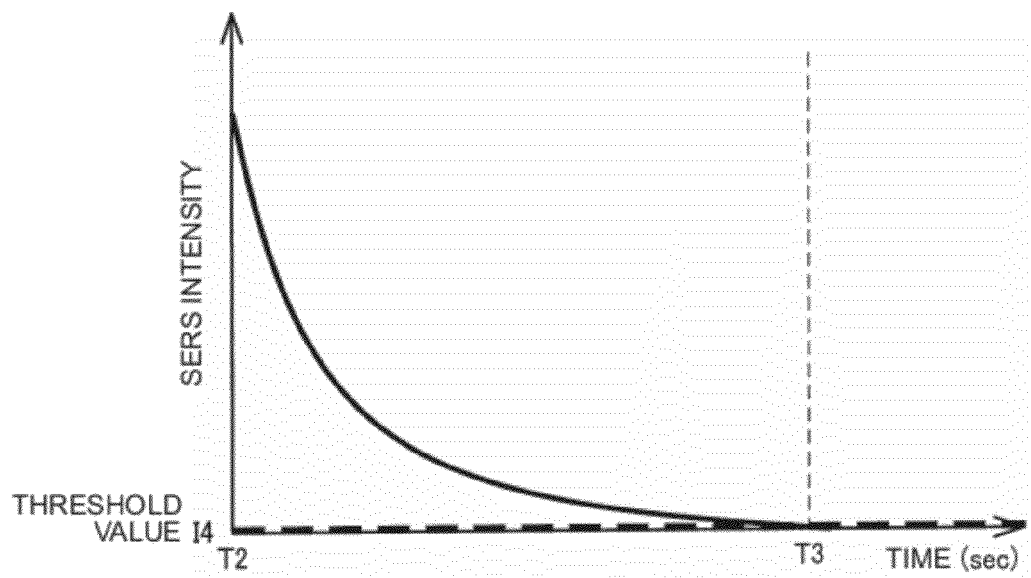
FIG. 15 is a characteristic diagram showing a variation in the spectral intensity of the reference molecules in the second mode.

FIG. 15 similarly shows the variation in the SERS intensity of the reference molecules as the output of the light detection section 60 in the second mode (the breakaway mode). In the second mode started at the time T2, the amount of the reference molecules breaking away from the optical device 20 increases since no reference molecules are supplied, and moreover, the flow velocity is high. Therefore, the SERS intensity decreases in the second mode. Therefore, it is possible to end the second mode at the time T3 at which the SERS intensity falls below a fourth threshold level I4 shown in FIG. 15.

Here, the reference molecules can be composed of the molecules including at least one of a hetero ring, a benzene ring, a COOH group, an OH group, a CHO group, an S atom, and an N atom. For example, pyridine can be cited as an example of the hetero ring. In the case in which the TNT having the peak in the vicinity of 800 $cm^{-1}$ is set to the sample molecules, since the pyridine as the reference molecules has acute peaks at 1010 $cm^{-1}$ and 1035 $cm^{-1}$, the peaks of the Raman scattering light do not overlap with each other.

5.2. Third Experimental Example

Figure 16:
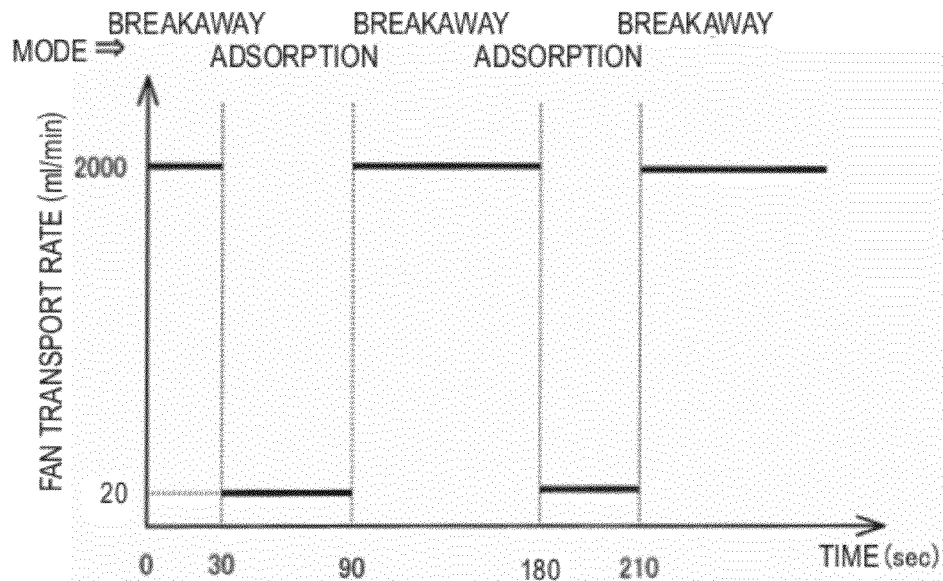
FIG. 16 is a time chart of the first and second modes switched based on detection of the reference molecules in a third experimental example.
Figure 17:
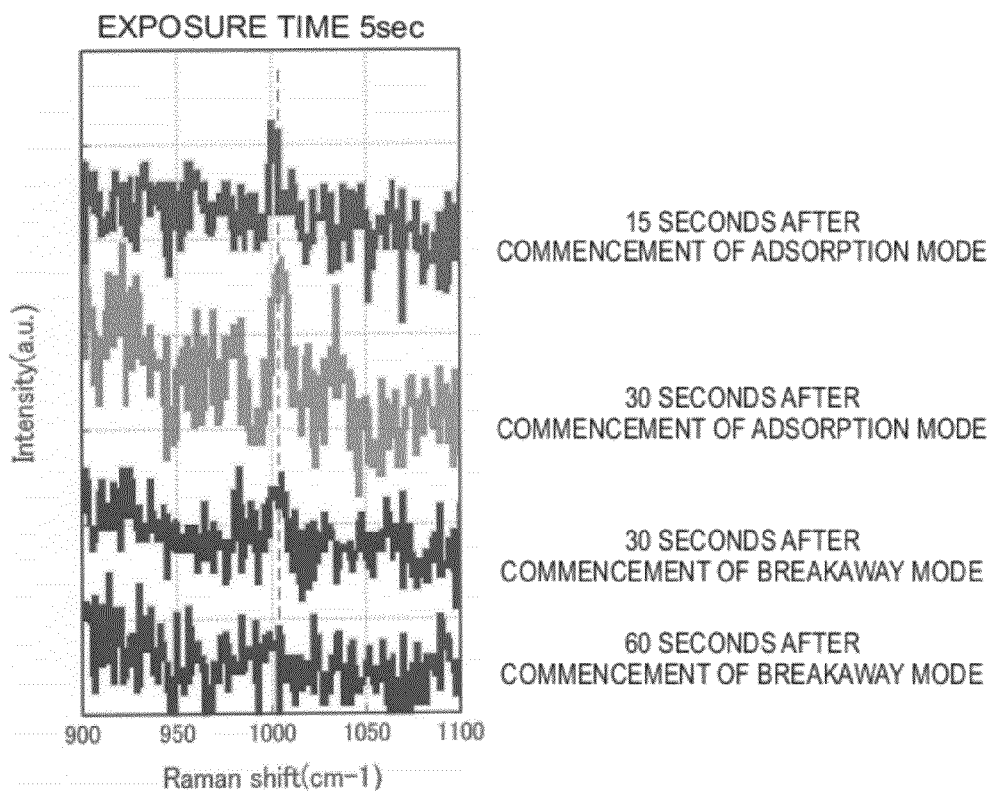
FIG. 17 is a characteristic diagram showing a measurement result of the reference molecules in the third experimental example.

FIG. 17 shows a result of an actual measurement using pyridine molecules as the reference molecules performed in accordance with the time chart of the first mode (the adsorption mode) and the second mode (the breakaway mode) shown in FIG. 16. It should be noted that the sample molecules are not particularly assumed in the third experimental example. As the light source 50 shown in FIG. 6, a He—Ne laser with an excitation wavelength of 632.8 nm and intensity of 2 mW is used. The measurement exposure time in the light detection section 60 shown in FIG. 6 is set to 10 seconds, and the material of the optical device 20 shown in FIG. 6 is Ag. The fluid transport rate L1 of the fan 450 in the first mode (the adsorption mode) is set to 20 ml/min, and the fluid transport rate L2 of the fan 450 in the second mode (the breakaway mode) is set to 2000 ml/min.

As shown in FIG. 16, the experiment starts with the breakaway mode for 30 seconds. The mode is switched to the adsorption mode of L1: 20 ml/min, 30 seconds later. The supply of the pyridine as the reference molecules is started immediately after the switching, and the supply time is set to 10 seconds. FIG. 17 shows the SERS spectrum of the pyridine molecules thus measured.

In FIG. 17, the peak of the pyridine molecules in the vicinity of 1010 $cm^{-1}$ can clearly be recognized at both timings 15 seconds and 30 seconds after the commencement of the adsorption mode.

Subsequently, the mode is switched to the breakaway mode of L2: 2000 ml/min, the breakaway is promoted. The attenuation is observed in the spectrum measured 30 seconds after the commencement of the breakaway mode, and the significant attenuation occurs 60 seconds after the commencement of the breakaway mode. It should be noted that the time described here is nothing more than an example, and needs to appropriately be changed with the material of the optical device, the sample molecules, and the reference molecules.

In the experimental example shown in FIG. 16, although the initial breakaway mode is set to 30 seconds, the subsequent adsorption mode is set to 60 seconds, and the further breakaway mode is set to 90 seconds, in reality, as shown in FIGS. 14 and 15, the mode switching is performed by comparing the SERS intensity of the reference molecules with the third threshold level I3 and the fourth threshold level I4.

6. Other Modified Examples

It should be noted that although the present embodiment is hereinabove explained in detail, it can easily be understood by those skilled in the art that various modifications not substantially departing from the novel matters and the effects of the invention are possible.

Figure 18:
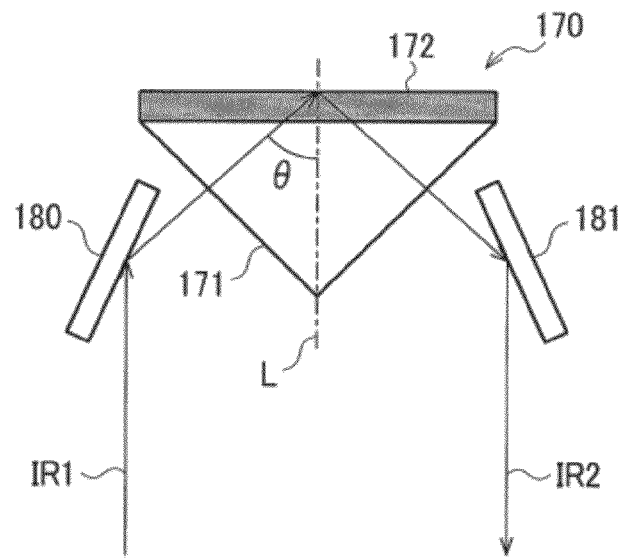
FIG. 18 is a schematic explanatory diagram of an optical device used for a surface-enhanced infrared spectroscopy.

The invention is not limited to those detecting the SERS intensity. For example, surface enhanced infrared absorption spectroscopy (SEIRAS) can be used. In this case, the optical device 20 shown in one of FIGS. 1, 6, and 13 is replaced with the optical device 170 shown in FIG. 18. The optical device 170 is obtained by forming a metal thin film 172 on, for example, the bottom surface of a rectangular prism 171. The rectangular prism 171 is made of a material such as $CaF_2$ transmitting an infrared ray. The material of the metal thin film 172 can be a metal thin film made of Ag, Cu, or the like.

Figure 19:
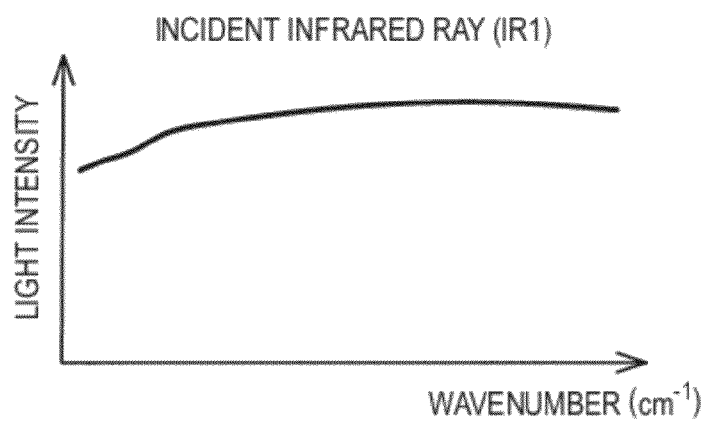
FIG. 19 is a characteristic diagram of an infrared ray entering the optical device shown in FIG. 18.
Figure 20:
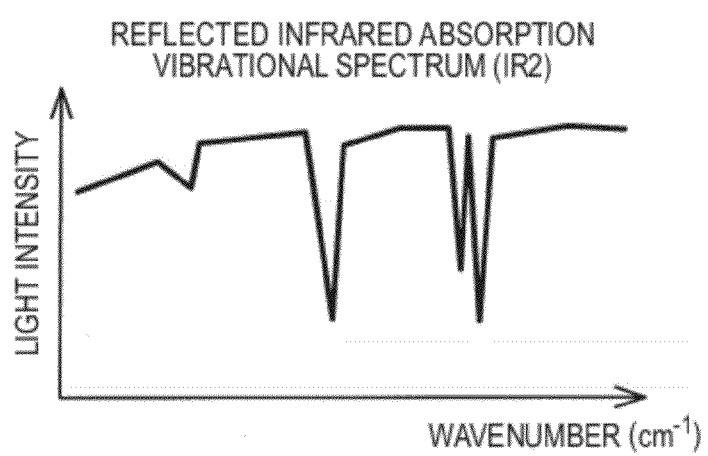
FIG. 20 is a characteristic diagram of the infrared ray reflected by the optical device shown in FIG. 18.

An infrared ray IR1 with P polarized light having the characteristics shown in FIG. 19 is input to the optical device 170 at an angle θ with respect to the normal line L of the metal thin film 172 after being reflected by, for example, a first reflecting mirror 180. In the reflected infrared ray IR2 obtained by making the incident infrared ray IR1 be totally reflected by the metal thin film 172, there exists an evanescent wave reflected at a position getting into the boundary toward the sample side, and thus the spectrum of the sample molecules and the reference molecules can be measured. FIG. 20 shows the characteristics of the reflected infrared ray IR2. The reflected infrared ray IR2 is reflected by a second reflecting mirror 181, and is input to the light detection section 60 shown in FIG. 6 and so on.

The entire disclosure of Japanese Patent Application No. 2011-085927, filed Apr. 8, 2011 is expressly incorporated by reference herein.

What is claimed is:

1. A detection device comprising:
   an optical device, wherein the optical device emits light based on an inspection target material that exists within a fluid sample, wherein the inspection target material is adsorbed onto a surface of the optical device;
   a suction section adapted to suck the fluid sample in the optical device;
   a light source adapted to irradiate the optical device with light;
   a light detection section adapted to detect light emitted from the optical device; and
   a control section adapted to perform drive control on the suction section,
   wherein the control section sets a suction flow velocity of the fluid sample in the optical device to V1 in a first mode including a period of performing detection by the light detection section, sets the suction flow velocity of the fluid sample on the optical device to V2, where V2>V1, in a second mode, and switches between the first mode and the second mode based on a signal from the light detection section,
   wherein the emitted light is a Raman scattering light of the inspection target material within the fluid sample,
   the light detection section detects the Raman scattering light of the inspection target material,
   the control section performs switching from the first mode to the second mode in response to a level of the signal from the light detection section exceeding a first threshold level,
   the control section performs switching from the second mode to the first mode in response to the level of the signal from the light detection section falling below a second threshold level lower than the first threshold level,
   the first mode is an adsorption mode wherein an external force generated by the suction section is less than an adsorption force between the inspection target material and the surface of the optical device, and the second mode is a break away mode in which the external force generated by the suction section is greater than the adsorption force between the inspection target material and the surface of the optical device.

2. The detection device according to claim 1, wherein the optical device is provided with a metal nanostructure having projections in a range of 1 through 1000 nm.

3. The detection device according to claim 1, wherein the suction section includes a negative pressure generation section, and the control section performs adjustment control of a drive condition of the negative pressure generation section.

4. The detection device according to claim 1, wherein the control section turns off the negative pressure generation section in the first mode.

5. The detection device according to claim 1, further comprising:

a supply section adapted to supply the optical device with a reference sample in the first mode, wherein the light detection section detects a signal reflecting the reference sample at a wavelength different from that of the inspection target material within the fluid sample, and the control section performs switching from the first mode to the second mode in response to a level of the signal reflecting the reference sample exceeding a third threshold level despite the signal reflecting the inspection target material is lower than the first threshold level.

6. The detection device according to claim 5, wherein the control section performs switching from the second mode to the first mode in response to a level of the signal reflecting the reference sample falling below a fourth threshold level lower than the third threshold level despite the level of the signal reflecting the inspection target material is higher than the second threshold level.

7. The detection device according to claim 5, wherein the supply section supplies a constant amount of the reference sample during the first mode.

8. The detection device according to claim 5, wherein the reference sample is a molecule including at least one of a hetero ring, a benzene ring, a COOH group, an OH group, a CHO group, an S atom, and an N atom.

9. The detection device according to claim 1, wherein the control section performs switching in order of the second mode, the first mode, and the second mode.

* * * * *